United States Patent
Matthis et al.

(10) Patent No.: US 8,216,274 B2
(45) Date of Patent: Jul. 10, 2012

(54) LONGITUDINAL MEMBER FOR USE IN SPINAL OR TRAUMA SURGERY AND STABILIZATION DEVICE WITH SUCH A LONGITUDINAL MEMBER

(75) Inventors: Wilfried Matthis, Weisweil (DE); Lutz Biedermann, VS-Villingen (DE)

(73) Assignee: Biedermann Technologies GmbH & Co. KG, Donaueschingen (DE)

( * ) Notice: Subject to any disclaimer, the term of this patent is extended or adjusted under 35 U.S.C. 154(b) by 885 days.

(21) Appl. No.: 11/749,395

(22) Filed: May 16, 2007

(65) Prior Publication Data

US 2007/0270843 A1  Nov. 22, 2007

Related U.S. Application Data

(60) Provisional application No. 60/800,986, filed on May 16, 2006.

(30) Foreign Application Priority Data

May 16, 2006  (EP) .................................... 06010070

(51) Int. Cl.
*A61B 17/70* (2006.01)
(52) U.S. Cl. ................... 606/246; 606/254; 606/264
(58) Field of Classification Search .................. 606/61, 606/86 A, 86, 103, 246–279, 300–321; *A61B 17/70*
See application file for complete search history.

(56) References Cited

U.S. PATENT DOCUMENTS

| 4,653,481 | A | * | 3/1987 | Howland et al. .............. 606/261 |
| 4,968,317 | A | * | 11/1990 | Tormala et al. ................. 606/77 |
| 5,431,652 | A | | 7/1995 | Shimamoto et al. |
| 5,545,165 | A | * | 8/1996 | Biedermann et al. ......... 606/261 |
| 5,591,165 | A | * | 1/1997 | Jackson ......................... 606/264 |
| 5,725,527 | A | * | 3/1998 | Biedermann et al. ......... 606/270 |
| 6,280,474 | B1 | * | 8/2001 | Cassidy et al. ............. 623/16.11 |
| 6,652,526 | B1 | * | 11/2003 | Arafiles ........................ 606/308 |
| 6,964,665 | B2 | * | 11/2005 | Thomas et al. ............. 606/86 A |
| 6,989,011 | B2 | * | 1/2006 | Paul et al. ..................... 606/250 |

(Continued)

FOREIGN PATENT DOCUMENTS

EP  1 364 622 A2  11/2003

(Continued)

OTHER PUBLICATIONS

European Search Report, dated Nov. 15, 2006, Application No. EP 06 01 0070.8-2318; Place of Search: Munich; Date of Completion of the Search Nov. 6, 2006; (5 pages).

*Primary Examiner* — Eduardo C Robert
*Assistant Examiner* — Christina Negrelli
(74) *Attorney, Agent, or Firm* — Christie, Parker & Hale, LLP

(57) ABSTRACT

A longitudinal member for use in spinal or trauma surgery is provided which is sized to span a distance between at least two vertebrae or two bone parts, wherein the longitudinal member is made at least partially of a polymer material, such as an elastomer, which is extruded. The polymer chains of the longitudinal member are substantially aligned in the longitudinal direction of the member. The longitudinal member is included in a dynamic stabilization device having at least two bone anchoring elements and such a longitudinal member connecting the bone anchoring elements.

5 Claims, 4 Drawing Sheets

U.S. PATENT DOCUMENTS

| | | |
|---|---|---|
| 7,491,208 B2 * | 2/2009 | Pond et al. .................. 606/104 |
| 2003/0220642 A1 | 11/2003 | Freudiger |
| 2004/0215191 A1 * | 10/2004 | Kitchen ........................ 606/61 |
| 2005/0033295 A1 | 2/2005 | Wisnewski |
| 2005/0096659 A1 | 5/2005 | Freudiger |
| 2005/0203517 A1 * | 9/2005 | Jahng et al. .................... 606/61 |
| 2005/0277922 A1 * | 12/2005 | Trieu et al. ..................... 606/61 |

FOREIGN PATENT DOCUMENTS

| | | |
|---|---|---|
| EP | 1 527 742 A1 | 5/2005 |
| JP | 05-168647 | 7/1993 |
| JP | 11-192298 | 7/1999 |
| WO | WO 88/05312 | 7/1988 |

* cited by examiner a)   b)   c)   g)

d)   e)   f)

LONGITUDINAL MEMBER FOR USE IN SPINAL OR TRAUMA SURGERY AND STABILIZATION DEVICE WITH SUCH A LONGITUDINAL MEMBER

CROSS-REFERENCE TO RELATED APPLICATION(S)

The present application claims the benefit of U.S. Provisional Patent Application Ser. No. 60/800,986, filed May 16, 2006, and claims priority from European Patent Application EP06010070.8, filed May 16, 2006, the entire disclosures of which are incorporated herein by reference.

BACKGROUND

The present application relates to a longitudinal member for use in spinal or trauma surgery and a stabilization device with such a longitudinal member.

A dynamic stabilization system for segments of the spinal column which comprises a flexible rod made of an elastic material and bone anchors to anchor the rod in the vertebrae is known from EP 1 364 622 A2 and EP 1 527 742 A1, respectively. The material of the rod is a biocompatible polymer material, for example a material on the basis of polyurethane. The rod has a corrugated surface with the corrugations extending in a direction transverse to the rod axis.

Usually, the elastic rods are manufactured by injection molding whereby the molten plastic material is injected at high pressure into a mold which is the inverse of the desired shape. As shown in FIG. 1, after injection molding, the polymer chains 100 of the material are entangled and may include filling particles 101 and transverse links 102 between them. A rod 103 which is made by injection molding comprises an isotropic structure of the polymer chains and is therefore non homogeneous in a sense that it comprises defects in its macromolecular structure. The known elastomer rods exhibit a local flow of material when pressure is exerted onto their surface in the process of fixing the rod within a receiving part of a bone anchoring element. This local flow of material may cause a loosening of the fixation of the rod within the bone anchoring element.

Based on the above, there is a need to provide a longitudinal member for use in spinal or trauma surgery and a stabilization device using such a longitudinal member manufacturing which has improved mechanical properties as well as reduced manufacturing costs compared to the known polymer rods.

SUMMARY

A longitudinal member or a rod according to aspects of the disclosure has the advantage that its tendency to flow when being fixed to the bone anchor is reduced in comparison to the known injection molded elastomer rods. In addition, the longitudinal member in form of the extruded elastomer rod exhibits a lower permanent set, which characterizes the deformation remaining after removal of the deforming stress, and a higher stiffness characterized by the e-modulus compared to the injection molded rod at identical dimensions of the rod. Therefore, under identical load conditions, an extruded elastomer rod with smaller dimensions can be used. Furthermore, the strength against mechanical tensile and/or compressive loads and the abrasion resistance is enhanced. The costs for manufacturing are reduced with regard to the necessary tools and machines which are less expensive compared to the costs for the manufacturing by injection molding.

The rod can be cut to the desired length before or during surgery.

Further features and advantages of the disclosure will become apparent and will be best understood by reference to the following detailed description of embodiments taken in conjunction with the accompanying drawings

DETAILED DESCRIPTION

Figure 3:
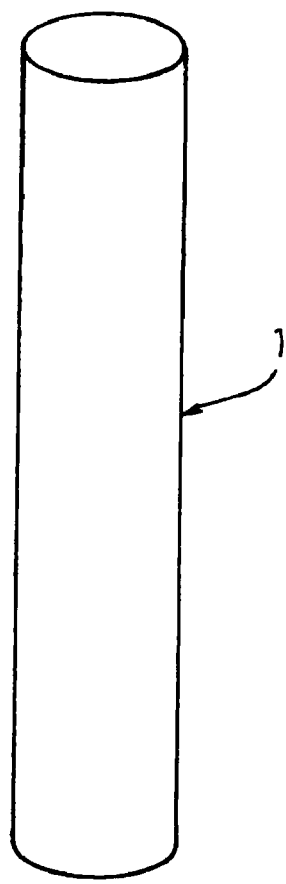
FIG. 3 shows a perspective view of a rod according to the present disclosure.
Figure 4:
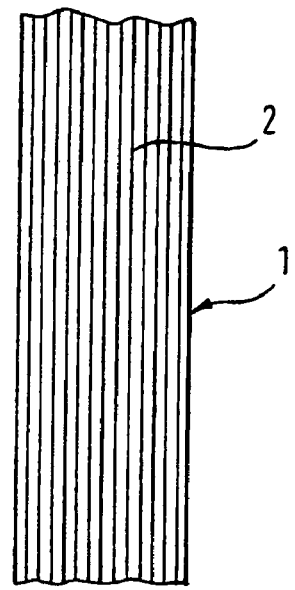
FIG. 4 shows a schematic cross-sectional view of the rod according to FIG. 3 in a plane including the longitudinal axis of the rod.
Figure 5:
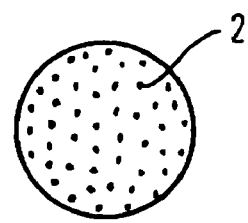
FIG. 5 shows a schematic cross-sectional view of the rod according to FIG. 3 in a plane perpendicular to the longitudinal axis.
Figure 6:
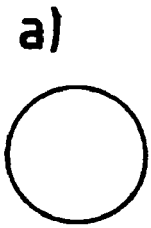
FIGS. 6a-6g show examples of cross-sections of the rod.
Figure 6:
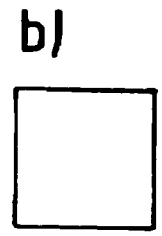
Figure 6:
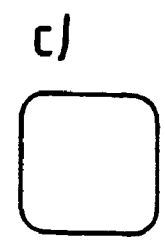
Figure 6:
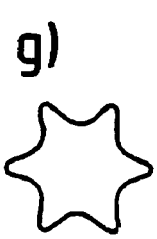
Figure 6:
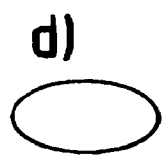
Figure 6:
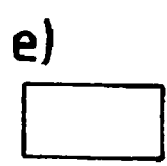
Figure 6:

FIGS. 3 to 5 show an embodiment of the disclosure used as a spinal rod 1. The rod has a substantially circular cross section and a length which is suitable to span a distance between at least two vertebrae. The diameter of the rod can be selected so as to be compatible with that of known metallic spinal rods. In this case, the rod 1 can be connected to known bone screws. In the embodiment shown the cross-section of the rod is constant over the length of the rod.

The rod is made of a biocompatible plastic material which can be molded by extrusion. For example, the material can be a thermoplastic material such as polyaryletheretherketone (PEEK). Preferably, the material is flexible, such as an elastomer. Suitable elastomers are for example polymer materials on the basis of polyurethane, polycarbonate-urethane (PCU) or silicone. The rod exhibits a three-dimensional elasticity in such a way that a restoring force acts when the rod is put under load which restores the original shape of the rod.

As can be seen in particular in FIGS. 3 and 4, the macromolecular construction of the rod 1 is characterized by polymer chains 2 of the elastomer material which are substantially aligned in the longitudinal direction of the rod 1. The macromolecular structure of the rod is therefore substantially uniform in the longitudinal direction. The polymer chains 2 form a fiber-like structure with the fibers oriented in the longitudinal direction, thus being load oriented.

The rod 1 is preferably manufactured by extrusion. In the well known manufacturing process of extrusion, the solid or fluid raw material is filled in an extruder and then pressed through an opening. The parameters such as temperature and pressure during the extrusion process depend on the material used and will be recognized by those skilled in the art.

Figure 1:
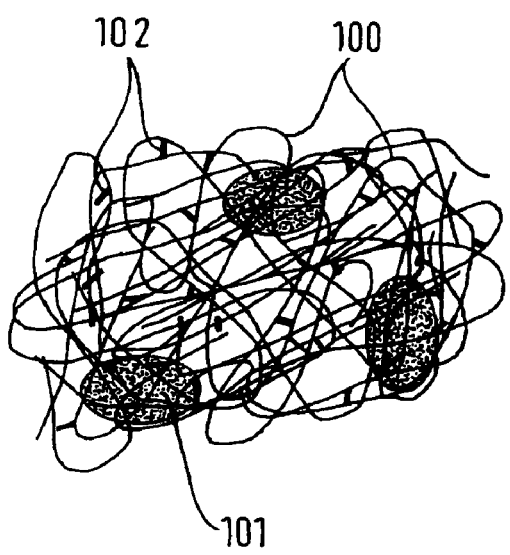
FIG. 1 shows a schematic representation of an arrangement of polymer chains of a polymer plastic material after injection molding.
Figure 2:
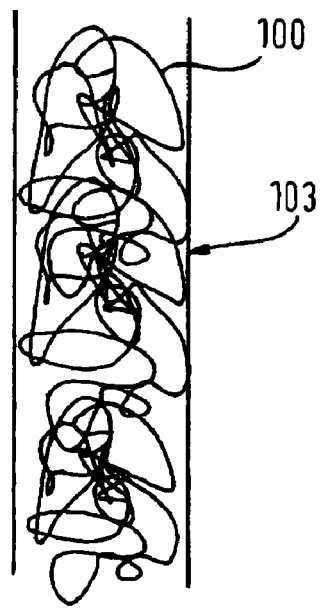
FIG. 2 shows a schematic cross-section of a spinal rod made of a polymer plastic material produced by injection molding.

Hence, the rod 1 can be distinguished from a conventional rod made of the same material but manufactured for example by injection molding, as shown in FIG. 2. The extruded rod has enhanced mechanical strength compared to a rod made of the same material by means of injection molding. For example, the strength against mechanical tensile and/or compressive loads is enhanced. Furthermore, the wear resistance is enhanced. Therefore, the rod implant has an improved lifetime.

The rod can have other shapes than a circular cross section. As can be seen in FIGS. 6a to 6g, different cross sections such as circular (FIG. 6a), square (FIG. 6b), rounded square (FIG. 6c), oval-shaped (FIG. 6d), rectangular (FIG. 6e), rounded rectangular (FIG. 6f) or star-shaped (FIG. 6g) or triangular are possible. Preferably the cross-section is constant over the length of the rod. With a non-circular cross-section of the rod, a rotation of the rod in the bone anchoring element to which it is connected can be prevented. In addition, the shape of the cross-section can be used to achieve bending properties in flexion/extension movement and lateral bending which can differ from each other.

Figure 7:
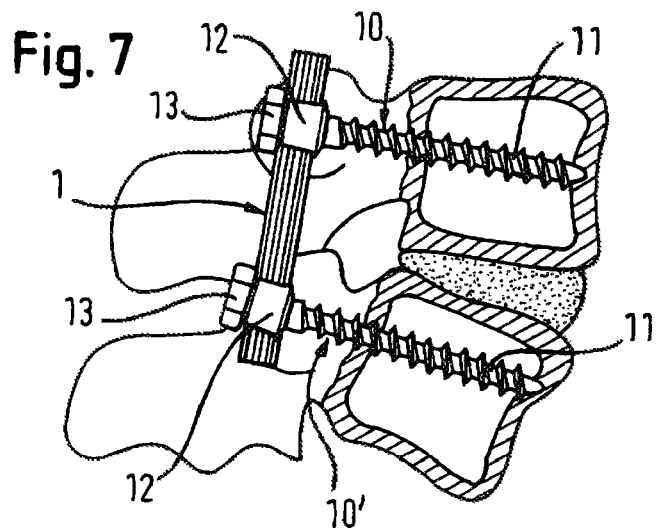
FIG. 7 shows a stabilization device for the spinal column including a rod according to the disclosure and two monoaxial bone screws.

A stabilization device using the rod according to the disclosure comprises at least two bone anchoring elements for connection of the rod to the bone. As can be seen in FIGS. 7 and 8, according to a first example, the bone anchoring elements are monoaxial bone screws 10, 10' each comprising a threaded shaft 11 which is to be anchored in a vertebra and a receiving part 12 which is rigidly connected to the threaded shaft. The receiving part 12 has a substantially U-shaped recess to receive the rod 1. A locking element, for example an inner screw to be screwed into the recess or, as shown, an outer nut 13 is provided to fix the rod 1 in the recess. The bone anchoring elements are made of a biocompatible rigid material, for example of a biocompatible metal, such as titanium or a metal alloy.

In use, first, the bone anchoring elements 10, 10' are screwed into the vertebrae which shall be stabilized. Then the rod 1 is inserted into the receiving parts 12 and, after adjustment of its position, fixed in the receiving part by means of the locking element 13. Due to the uniformly aligned macromolecular structure of the rod the tendency to flow under pressure of the locking element is reduced. Therefore, the risk of loosening of the fixation between the rod and the bone anchoring element is reduced. Since the rod exhibits elasticity under flexion, extension and torsion of the spinal segment, the spinal segment can be dynamically stabilized. The elasticity required for a certain application can be obtained by selecting the material and/or the size and/or the shape of the cross-section of the extruded rod.

In the stabilization device of FIG. 7 the rod 1 is used in a straight state. The vertebral segment can perform a limited motion in all planes controlled by the elasticity of the rod.

Figure 8A:
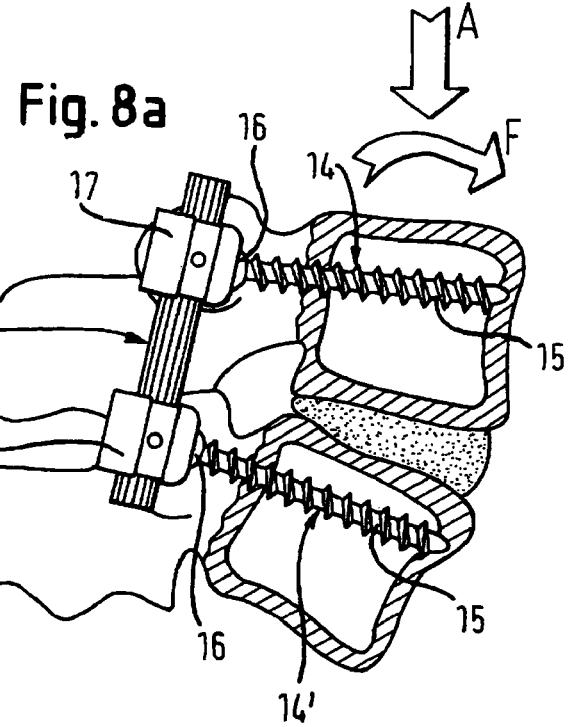
FIG. 8a shows a stabilization device for the spinal column including a rod according to the disclosure and two polyaxial bone screws.

FIG. 8a shows a second example of a stabilization device using the extruded rod 1. The stabilization device has at least two polyaxial bone anchoring elements 14 and 14' having a threaded shaft 15 to be anchored in the bone and a spherically-shaped head 16 at one end. The head 16 is pivotably held in a receiving part 17 which also receives the rod 1 in a recess. Preferably, a pressure element (not shown) is provided which presses onto the head to fix the head in the receiving part in its angular position. A locking element (not shown) is also provided to fix the rod in the recess.

In use, like in the first example, the bone anchoring elements 14 and 14' are screwed into the vertebrae and thereafter the rod 1 is inserted. Since the head 16 is pivotably held in the receiving part 17 the position of the receiving parts can be adjusted relative to the heads. After adjustment of the position of the receiving parts relative to the heads and of the rod relative to the receiving part, the connection is locked by means of the locking element.

Figure 8B:
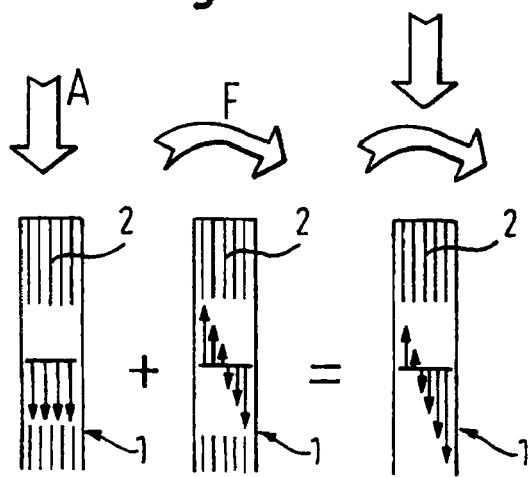
FIG. 8b schematically shows the forces acting onto the rod under axial load and flexion.

FIG. 8b schematically shows the forces acting onto the rod under axial (A) and flexural (F) load during motion of the spinal segment shown in FIG. 8a. As can be seen, the force components of the axial and flexural load are mainly oriented in the direction of the alignment of the polymer chains 2. This renders the extruded rod particularly suitable for the application in dynamic stabilization of the spinal column. This also applies to the stabilization device shown in FIG. 7 using monoaxial screws.

Figure 9:
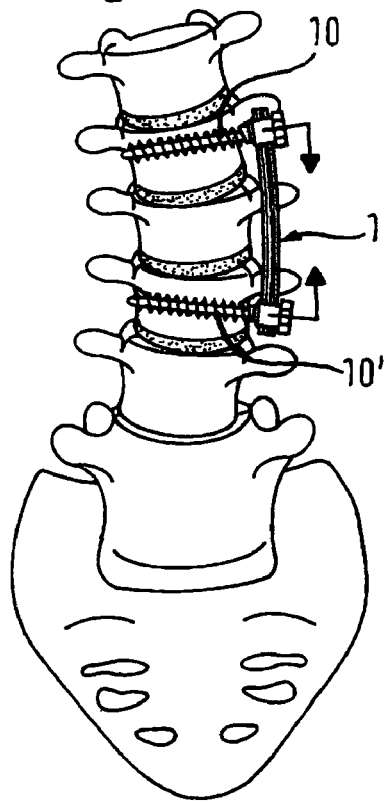
FIG. 9 shows application of the stabilization device according to the disclosure to the spinal column for the purpose of correction of scoliosis, wherein the rod according to the disclosure is in a first, pre-stressed condition.
Figure 10:
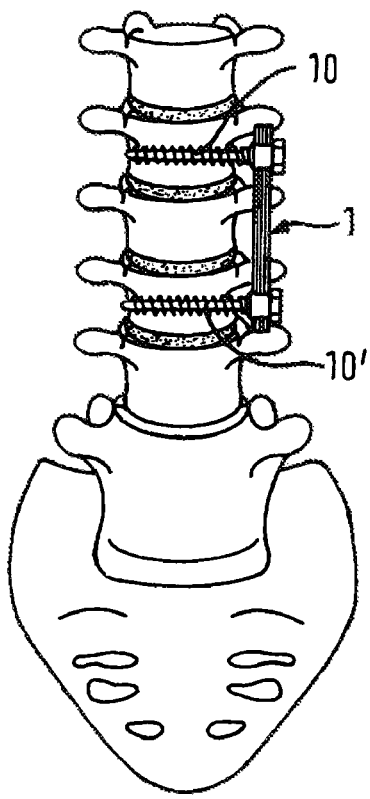
FIG. 10 shows the stabilization device of FIG. 9 in a second condition.

FIGS. 9 and 10 show an example of a clinical application of a correction device. The correction device which includes two bone anchoring elements 10 and the extruded rod 1 is applied to a spinal section exhibiting scoliosis. The elastic rod is bent out of its neutral straight shape so as to be adapted to the curvature of the spinal deformity as shown in FIG. 9. By narrowing the distance between the screw heads of the correction device as indicated by the arrows in FIG. 9, a pretension is generated in the rod which urges the deformed part of the spine into a straight position as shown in FIG. 10. For the bone anchoring elements monoaxial or polyaxial screws can be used. Polyaxial screws have the advantage that the shaft and the head can be aligned for receiving the rod.

Figure 11:
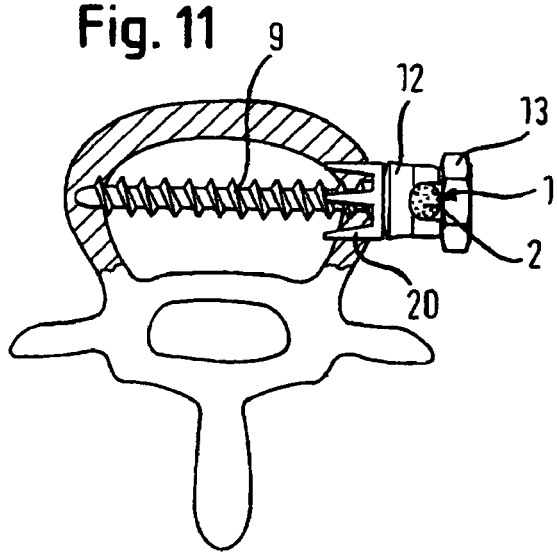
FIG. 11 is a schematic view showing a bone screw and a clamp anchored in a vertebra and fixing the rod.

FIG. 11 shows a schematic view in the direction of the longitudinal axis of the spine of one bone anchoring element anchored in a vertebra. The extruded rod is clamped in the receiving part 12 by the locking element 13. The polymer chains 2 are substantially aligned in the longitudinal direction of the rod. If required, additional fixation in the bone can be provided by means of clamps 20.

Figure 12:
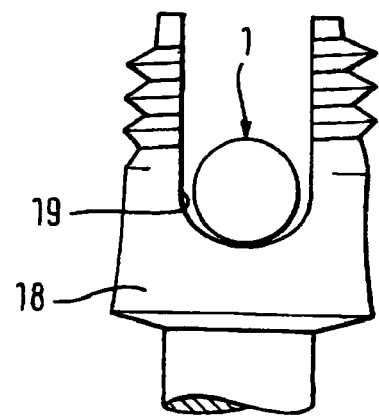
FIG. 12 shows a modified example of a bone anchoring element receiving the rod.

FIG. 12 shows a modified example of a bone anchoring element with the rod inserted into the recess of the receiving part. The receiving part 18 comprises a recess 19 with a crosssection which differs from the cross-section of the rod. In the example shown the cross section of the recess is ovalshaped while the cross-section of the rod is circular with a diameter smaller that of the recess. Fixation can be achieved via a locking element (not shown) either directly or with a filling piece (not shown) between the locking element and the rod.

The disclosure is not limited to the above described embodiments and examples of application. The features of the examples described can be combined with each other. Although the rod is shown to connect two bone anchoring elements, it can have a length sufficient to connect more than two bone anchoring elements. Since the rod is made of an elastomer, the length can be adapted before or at the time of surgery by cutting the rod.

The rod can be made fully or partially of the polymer material. For certain applications it is sufficient that a section of the whole rod is made of extruded polymer material. The length of the section depends on the specific application and the required flexibility. A non isotropic shape for the cross-section, such as for example a rectangular shape, can be used for providing a rod with elastic characteristics which differ dependent on the direction.

The rod can be hollow and can include a core in its hollow interior for obtaining further characteristics.

With the manufacturing method of extrusion it is possible to produce rods with different shapes and diameters of the crosssection at low costs, since it is not necessary to use complex molds and expensive machines like in the injection molding process.

For the bone anchoring elements all known types can be used which are typically used with the known metallic rods.

The disclosure is also not limited to the application for the spine. The rod can also be used in stabilizing a fractured bone, for example instead of a metallic rod in a fixateur externe or interne.

The term polymer material as described above means a single polymer material or mixtures of polymer materials including co-polymers and so-called block co-polymers having hard and soft segments. It also includes polymer materials with additions such as filling particles or strengthening fibres like carbon fibres or the like. Strengthening fibers can be used to enhance the stiffness, if required.

While a particular form of the disclosure has been illustrated and described, it will be apparent that various modifications can be made without departing from the spirit and scope of the disclosure. Accordingly, it is not intended that the disclosure be limited, except as by the appended claims.

What is claimed is:

1. A stabilization device for stabilizing vertebrae or bone parts, comprising:
   a longitudinal member for use in spinal or trauma surgery which is sized to span a distance in a longitudinal direction between at least two vertebrae or two bone parts, the entire longitudinal member having bending and axial elasticity, wherein the entire longitudinal member is a solid rod having a uniform cross-section and made of an elastomer material having fibers generally oriented in the longitudinal direction, wherein polymer chains of the elastomer material are substantially aligned in the longitudinal direction of the longitudinal member; and
   at least two bone anchoring elements, each anchoring element having a shaft for anchoring to the bone and a receiving part for connection with the longitudinal member.

2. The longitudinal member of claim 1, wherein the longitudinal member is manufactured by extrusion.

3. The longitudinal member of claim 1, wherein said elastomer material comprises a polymer on the basis of any one of polyurethane, polycarbonate-urethane and silicone.

4. The longitudinal member of claim 1, wherein the cross-section is substantially circular.

5. The stabilization device of claim 1, wherein the receiving part comprises a U-shaped recess for receiving the longitudinal member, a cross-section of a bottom part of the recess receiving the longitudinal member being different from a cross section of the longitudinal member.

* * * * *